US011083758B2

(12) United States Patent
Lucey et al.

(10) Patent No.: US 11,083,758 B2
(45) Date of Patent: Aug. 10, 2021

(54) PLACENTAL MEMBRANE PREPARATIONS AND METHODS OF MAKING AND USING SAME FOR REGENERATING CARTILAGE AND SPINAL INTERVERTEBRAL DISCS

(71) Applicant: Prime Merger Sub, LLC, Birmingham, AL (US)

(72) Inventors: Stephen Lucey, Greensboro, NC (US); Samuel K. Tabet, Albuquerque, NM (US); Jack Farr, II, Greenwood, IN (US); John J. Anderson, Alamogordo, NM (US); Katie C. Mowry, Birmingham, AL (US); Gregory J. Yager, Mount Olive, AL (US); Howard P. Walthall, Jr., Chestnut Hill, MA (US)

(73) Assignee: Prime Merger Sub, LLC, Birmingham, AL (US)

( * ) Notice: Subject to any disclaimer, the term of this patent is extended or adjusted under 35 U.S.C. 154(b) by 0 days.

(21) Appl. No.: 14/712,156

(22) Filed: May 14, 2015

(65) Prior Publication Data
US 2015/0328264 A1    Nov. 19, 2015

Related U.S. Application Data

(60) Provisional application No. 61/993,114, filed on May 14, 2014.

(51) Int. Cl.
| | | |
|---|---|---|
| *A61K 35/50* | (2015.01) | |
| *A61K 35/32* | (2015.01) | |
| *A61K 35/28* | (2015.01) | |
| *A61F 2/44* | (2006.01) | |
| *A61K 31/728* | (2006.01) | |
| *A61F 2/14* | (2006.01) | |

(52) U.S. Cl.
CPC .............. *A61K 35/50* (2013.01); *A61F 2/146* (2013.01); *A61F 2/44* (2013.01); *A61K 31/728* (2013.01); *A61K 35/28* (2013.01); *A61K 35/32* (2013.01)

(58) Field of Classification Search
CPC ........ A61K 35/50; A61K 35/28; A61K 35/32; A61F 2/44
See application file for complete search history.

(56) References Cited

U.S. PATENT DOCUMENTS

| | | |
|---|---|---|
| 3,358,688 A | 12/1967 | Tanner, Jr. |
| 3,472,228 A | 10/1969 | Tanner, Jr. |
| 3,640,279 A | 2/1972 | Brown et al. |
| 5,004,468 A | 4/1991 | Atkinson |
| 5,612,028 A | 3/1997 | Sackier et al. |
| 6,063,094 A | 5/2000 | Rosenberg |
| 7,824,711 B2 | 11/2010 | Kizer et al. |
| 8,932,805 B1 * | 1/2015 | Brahm ................. C12N 5/0605 435/1.3 |
| 2003/0185823 A1 * | 10/2003 | Lum ..................... A61K 38/193 424/144.1 |
| 2003/0187515 A1 | 10/2003 | Hariri et al. |
| 2004/0161419 A1 | 8/2004 | Strom et al. |
| 2005/0196460 A1 * | 9/2005 | Malinin .............. A61L 27/3612 424/548 |
| 2013/0209425 A1 * | 8/2013 | Martinson .............. A61K 35/39 424/93.7 |
| 2016/0066563 A1 * | 3/2016 | Moscatello .......... A01N 1/0221 435/1.3 |

FOREIGN PATENT DOCUMENTS

WO    WO2012/11241 A2 *    8/2012

OTHER PUBLICATIONS

Falah et al. "Treatment of articular cartilage lesions of the knee" 2010, International Orthopaedics, vol. 34: 621-630.*
De Lara Janz et al. "Evaluation of Distinct Freezing Methods and Cryoprotectants for Human Amniotic Fluid Stem Cells Cryopreservation" (2012), J Biomed Biotech, vol. 2012, Article ID 649353: 1-10. (Year: 2012).*
Boo L, et al., A preliminary study of human amniotic membrane as a potential chondrocyte carrier, Malay Orthop J 3, 16-23 (2009).
Davis, JS, Skin transplantation with a review of 550 cases at the Johns Hopkins Hospital, John Hopkins Med J 15, 307 (1910).
Diaz-Prado SM, et al., Cell therapy and tissue engineering to regenerate articular cartilage, in Biomedical Engineering, Trends, Research and Technologies (Komorowska MA & Olsztynska-Janus S, eds.), pp. 193-216 (2011).
Diaz-Prado SM, et al., Potential use of the human amniotic membrane as a scaffold in human articular cartilage repair, Cell Tissue Bank 11, 183-195 (2010).
Fiorentino G., et al., Easy and Safe All-Inside Suture Technique for Posterior Horn Tears of Lateral Meniscus Using Standard Anteromedial and Anterolateral Portals. Arthroscopy Techniques, vol. 2, No. 4 Nov. 2013: pp. e355-e359.
Hildner F, et al., State of the art and future perspectives of articular cartilage regeneration: a focus on adipose-derived stem cells and platelet-derived products, J Tissue Eng Regen Med 5, e36-e51 (2011).
Jin CZ, et al., Human amniotic membrane as a delivery matrix for articular cartilage repair, Tiss Eng 13, 693-702 (2007).

(Continued)

*Primary Examiner* — Teresa E Knight
(74) *Attorney, Agent, or Firm* — C. Brandon Browning; Matthew Parker; Maynard, Cooper & Gale, PC

(57) ABSTRACT

A method for treating cartilage defects including providing a placental membrane preparation that includes ground or minced placental membranes and optionally, a ground or minced cartilage and/or biocompatible glue, and introducing the preparation to a cartilage defect within a skeletal joint. The cartilage defect may include a hyaline cartilage defect, such as a chondral defect, or meniscal defect. The treatment may be provided in combination with other treatments such as marrow stimulation treatments and surgical repair treatments using sutures or other fixation techniques. The preparation promotes the regeneration of cartilage within the skeletal joint.

37 Claims, No Drawings

(56) References Cited

OTHER PUBLICATIONS

Kanthan SR, et al., The different preparations of human amniotic membrane (HAM) as a potential cell carrier for chondrocytes, Eur Cell Mater 20, 1 page (2010).
Kon, E. et al., Tissue Engineering for Total Meniscal Substitution: Animal Study in Sheep Model—Results at 12 Months. Tissue Eng Part A. Aug. 2012;18(15-16):1573-82.
Krishnamurithy G, et al., Human amniotic membrane as a chondrocyte carrier vehicle/substrate: in vitro study, J Biomed Mater Res Part A 99A, 500-506 (2011).
Lindenmair A, et al., Osteogenic differentiation of intact human amniotic membrane, Biomaterials 31, 8659-8665 (2010).
Mermet I, et al., Use of amniotic membrane transplantation in the treatment of venous leg ulcers, Wound Repair and Regeneration 15, 459 (2007).
Mithoefer, K et. al., Chondral resurfacing of articular cartilage defects in the knee with the microfracture technique. Surgical technique. J Bone Joint Surg Am. Sep. 2006;88 Suppl 1 Pt 2:294-304.
Moriya T, et al., Evaluation of reparative cartilage after autologous chondrocyte implantation for osteochondritis dissecans: histology, biochemistry, and MR imaging, J Orthop Sci 12, 265-273 (2007).
Niknejad H, et al., Properties of the amniotic membrane for potential use in tissue engineering, Eur Cell Mater 15, 88-99 (2008).
Park, S.H., et. al., Intervertebral Disk Tissue Engineering Using Biphasic Silk Composite Scaffolds. Tissue Eng. Part A, (2012) 18(5-6):447-458.
Scotti C. et al., Meniscus Repair and Regeneration: Review on Current Methods and Research Potential. European Cells and Materials vol. 26 2013, 150-170.
Wilshaw SP, et al. Production of an acellular amniotic membrane matrix for use in tissue engineering, Tiss Eng 12, 2117-2129 (2006).
Xing, L. et al., Microfracture combined with osteochondral paste implantation was more effective than microfracture alone for full-thickness cartilage repair. Knee Surg Sports Traumatol Arthrosc (2013) 21:1770-1776.
Zhou S, et al., Demineralized bone promotes chondrocyte or osteoblast differentiation of human bone marrow stromal cells cultured in collagen sponges, Cell Tissue Bank 6, 33-44 (2005).

* cited by examiner

PLACENTAL MEMBRANE PREPARATIONS AND METHODS OF MAKING AND USING SAME FOR REGENERATING CARTILAGE AND SPINAL INTERVERTEBRAL DISCS

RELATED APPLICATION

This application claims priority to U.S. Provisional Application No. 61/993,114, filed on May 14, 2014 and titled "Placental Membrane Preparations and Methods of Making and Using Same for Regenerating Cartilage and Spinal Intervertebral Discs," the entire contents of which are incorporated herein by reference.

FIELD OF THE INVENTION

The present invention is directed to placental membrane preparations. More particularly, the present invention is directed to placental membrane preparations and methods of making and using same for regenerating articular cartilage and spinal intervertebral discs.

BACKGROUND OF THE INVENTION

The placenta surrounds a fetus during gestation and is composed of, among other tissues, an inner amniotic layer that faces the fetus and a generally inelastic outer shell, or chorion. The placenta anchors the fetus to the uterine wall, allowing nutrient uptake, waste elimination, and gas exchange to occur via the mother's blood supply. Additionally, the placenta protects the fetus from an immune response from the mother. From the placenta, an intact placental membrane comprising the amnion and chorion layers can be separated from the other tissues.

Clinicians have used intact placental membrane, comprising an amnion and a chorion layer, in medical procedures since as early as 1910 [Davis, J. S., *John Hopkins Med. J.* 15, 307 (1910)]. The amniotic membrane, when separated from the intact placental membrane, may also be used for its beneficial clinical properties [Niknejad H, et al. *Eur Cell Mater* 15, 88-99 (2008)]. Certain characteristics of the placental membrane make it attractive for use by the medical community. These characteristics include, but are not limited to, its anti-adhesive, anti-microbial, and anti-inflammatory properties; wound protection; ability to induce epithelialization; and pain reduction. [Mermet I, et al. *Wound Repair and Regeneration,* 15:459 (2007)].

Other uses for placental membrane include its use for scaffolding or providing structure for the regrowth of cells and tissue. An important advantage of placental membrane in scaffolding is that the amnion contains an epithelial layer. The epithelial cells derived from this layer are similar to stem cells, allowing the cells to differentiate into cells of the type that surrounds them. Multipotent cells similar to stem cells are also contained within the body of the amniotic membrane. Additionally, the amniotic membrane contains various growth and trophic factors, such as epidermal, insulin-like, and fibroblast growth factors, as well as high concentrations of hyaluronic acid, that may be beneficial to prevent scarring and inflammation and to support healing. Thus, placental membrane offers a wide variety of beneficial medical uses.

Cell-based therapies have considerable potential for the repair and regeneration of tissues. The addition of a scaffold to these cell-based therapies has yielded improved outcomes [Krishnamurithy G, et al. *J Biomed Mater Res Part A* 99A, 500-506 (2011)]. Ideally, the material used for the scaffold will be biocompatible such that it provokes little to no immune response, biodegrades, and is available in sufficient quantities to be practical. Although the placental membrane has long been identified as a material potentially filling this role in the clinic, efforts have been limited to in vitro studies, impractical in vivo techniques, or have yielded less than optimal outcomes. Furthermore, the conditions under which the scaffold is used may have a dramatic effect on the therapeutic efficacy.

While a number of placental membrane products have been studied in the literature or used clinically, these so far fall into two primary categories. The first category involves the use of the intact membrane, be it fresh, dried, freeze-dried, cryopreserved, or preserved in glycerol or alcohol. In this formulation, the membrane is useful for a number of purposes, but is not suitable for others, such as applications requiring injection, or the filling of a space which does not conform to the thin planar shape of the membrane itself.

The second category involves the grinding, pulverizing and/or homogenizing of the membrane into small particles, which may then be resuspended in solution. Such techniques are described, for example, in U.S. patent application Ser. Nos. 11/528,902; 11/528,980; 11/529,658; and 11/535,924. This grinding may be done dry or wet, and temperature during grinding may or may not be controlled, such as in the case of cryogrinding. Products produced using this method are useful for a number of applications, and may be injected under appropriate conditions. However, they have several deficiencies for certain applications. First, the cells contained in the placental membranes will be destroyed during the grinding process. Second, proteins and growth factors in the membrane may be leached out or lost during this process, including any subsequent washing or other treatment of the ground particles. Indeed, the removal of potentially angiogenic factors such as growth factors may be an objective of this type of processing. Third, resuspension of these small particles in typical physiologic solutions, such as saline, results in a free-flowing fluid with low viscosity. Upon injection or placement, this fluid may dissipate rather than remain in the desired treatment location. Fourth, the resulting fragments may not be large enough to permit cell engraftment and proliferation, if that is desired.

However, amniotic membrane preparations have been shown to have significant beneficial bioactivity. Many of the cells contained in these membranes are multi- or pluripotent. The membranes also contain a rich source of growth factors, as well as hyaluronic acid, collagen, and other factors which have been shown to support tissue healing. Amniotic membrane has been shown to attract and stimulate the proliferation of cells involved in tissue healing, such as mesenchymal stem cells and fibroblasts.

Articular cartilage, located on the articular ends of bones at joints throughout the body, is composed of hyaline cartilage and contains relatively few chondrocytes that are embedded in extracellular matrix materials, such as type II collagen and proteoglycans [Moriya T, et al. *J Orthop Sci* 12, 265-273 (2007)]. Articular cartilage has a limited ability to self-repair, in part due to the avascular characteristics of the cartilage, which poses a significant challenge to treating joint injuries or diseases. The repair of cartilage defects in humans can therefore be a difficult endeavor, and multiple options exist for the surgeon to approach this topic. The surgeon may choose to influence the defect with microfracture, abrasion or other marrow stimulation techniques which stimulate bleeding of the subchondral bone and the generation of a clot and ultimately a fibrocartilage patch which fills the defect. There are also options available that allow for the filling of the defect with chondrocytes of variable sources, both of autograft and allograft origin.

A key advantage of marrow stimulation techniques over most other available therapies is that marrow stimulation may be carried out arthroscopically using a relatively simple surgical technique, with minimal disruption to the joint and surrounding tissues. [Mithoefer, K et. al. Chondral resurfacing of articular cartilage defects in the knee with the microfracture technique. Surgical technique. *J Bone Joint Surg Am.* 2006 September; 88 Suppl 1 Pt 2:294-304]. The technique is also cost-effective. Efforts have therefore been made to improve the outcome of marrow stimulation techniques. Ground cartilage, either autograft or allograft (e.g. the product commercially marketed as BioCartilage) has been proposed for this purpose. [Xing, L. et al. Microfracture combined with osteochondral paste implantation was more effective than microfracture alone for full-thickness cartilage repair. *Knee Surg Sports Traumatol Arthrosc* (2013) 21:1770-1776]. However the use of autograft cartilage requires additional operative steps and donor site morbidity. The use of allograft cartilage alone has not been found to have satisfactory results.

Current treatments, including cell-based therapies, have resulted in the generation of undesirable fibrocartilaginous tissue rather than hyaline cartilage [Diaz-Prado S M, et al. BIOMEDICAL ENGINEERING, TRENDS, RESEARCH, AND TECHNOLOGIES, pp. 193-216 (2011)]. As such, there remains a significant clinical need for therapies capable of repairing damaged articular cartilage that are capable of regenerating hyaline-like cartilage.

A similar need exists for solutions for the repair of meniscal defects. A meniscus is a crescent-shaped fibrocartilaginous structure that, in contrast to articular disks, only partly divides a joint cavity. In humans they are present in the knee, acromioclavicular, sternoclavicular, and temporomandibular joints. Generally, the term 'meniscus' refers to the cartilage of the knee, either to the lateral and medial menisci. Both are cartilaginous tissues that provide structural integrity to the knee when it undergoes tension and torsion. They are concave on the top and flat on the bottom, articulating with the tibia. They are attached to the small depressions (fossae) between the condyles of the tibia (intercondyloid fossa), and towards the center they are unattached and their shape narrows to a thin shelf. The blood flow of the meniscus is from the periphery to the central meniscus. Blood flow decreases with age and the central meniscus is avascular by adulthood leading to very poor healing rates. Meniscal defects are repaired using sutures or other fixation approaches. Partial meniscectomies are also commonly used. [Kon, E. et al. Tissue Engineering for Total Meniscal Substitution: Animal Study in Sheep Model—Results at 12 Months. *Tissue Eng Part A.* 2012 August; 18(15-16):1573-82; Fiorentino G., et al. Easy and Safe All-Inside Suture Technique for Posterior Horn Tears of Lateral Meniscus Using Standard Anteromedial and Anterolateral Portals. Arthroscopy Techniques, Vol 2, No 4 (November), 2013: pp e355-e359; Scotti C. et al. Meniscus Repair And Regeneration: Review On Current Methods And Research Potential. European Cells and Materials Vol. 26 2013, 150-170].

Another related problem involves the regeneration of the human intervertebral disc. Intervertebral discs are fibrocartilaginous tissues occupying the space between vertebral bodies in the spine. They transmit forces from one vertebra to the next, while allowing spinal mobility. The structural properties of the disc are largely depending on its ability to attract and retain water. Proteoglycans in the disc exert an osmotic "swelling pressure" that resists compressive loads. Degeneration of the intervertebral disc is a physiologic process that is characteristic of aging in humans. With age, the disc undergoes a variety of changes, the most notable being a loss of proteoglycan content resulting in reduced osmotic pressure and a reduction in disc height and ability to transmit loads. [Park, S. H., et. al., Intervertebral Disk Tissue Engineering Using Biphasic Silk Composite Scaffolds. *Tissue Eng. Part A*, (2012) 18(5-6):447-458]. Disc degeneration is an important and direct cause of spinal conditions that account for most neck and back pain. As is the case with the related cartilage cells, components of the amniotic membrane may promote healing and recovery of the intervertebral disc and associated cells.

SUMMARY OF THE INVENTION

The present invention is directed to placental membrane preparations and methods of making and using same. In some embodiments, the placental membranes may be ground or minced using techniques known in the art, and combined with a biocompatible glue such as fibrin glue for cartilage repair or disc regeneration. Such membranes may be further combined with ground or minced autograft or allograft cartilage for implantation into a defect.

In another embodiment, ground membrane particles may be injected into the joint after marrow stimulation has been completed to stimulate the development of reparative cartilage. Such ground particles may be combined with prenatal stem cells, such as cells from the amniotic fluid or amniotic membrane, if desired. Such treatment may be repeated several times at subsequent time periods if desired.

In another embodiment, the invention is directed to a method of generating cartilage in vivo in a skeletal joint, the method including conducting a marrow stimulation procedure, and then placing in the defect a preparation of ground or minced amniotic membrane and a biocompatible glue. Ground or minced autograft or allograft cartilage may also be included. The cartilage that is generated may comprise, in whole or part, hyaline-like articular cartilage.

In another embodiment, the invention is directed to a method of regenerating a damaged meniscus, the method including removing any damaged meniscal tissue and filling the resulting void with an amniotic membrane preparation with or without the addition of biocompatible glue.

In another embodiment, the invention is directed to a method of regenerating a degenerated intervertebral disc, the method including inserting minced amniotic membrane into the disc, with or without the addition of biocompatible glue, and then closing any resulting opening in the disc using biocompatible glue or other closure means.

A further understanding of the nature and advantages of the present invention will be realized by reference to the remaining portions of the specification and the drawings of the present application.

DETAILED DESCRIPTION OF THE INVENTION

Before the present compositions, articles, devices, and/or methods are disclosed and described, it is to be understood that they are not limited to specific methods unless otherwise specified, or to particular reagents unless otherwise specified, and as such may vary. It is also to be understood that the terminology as used herein is used only for the purpose of describing particular embodiments and is not intended to be limiting.

This application references various publications. The disclosures of these publications, in their entireties, are hereby incorporated by reference into this application to describe more fully the state of the art to which this application pertains. The references disclosed are also individually and specifically incorporated herein by reference for material contained within them that is discussed in the sentence in which the reference is relied on.

A. DEFINITIONS

In this specification, and in the claims that follow, reference is made to a number of terms that shall be defined to have the following meanings:

As used herein, the singular forms "a," "an," and "the" include plural referents unless the context clearly indicates otherwise. Thus, for example, reference to "a pharmaceutical carrier" includes mixtures of two or more such carriers, and the like.

As used herein, ranges can be expressed as from "about" one particular value, and/or to "about" another particular value. When such a range is expressed, an embodiment includes from the one particular value and/or to the other particular value. Similarly, when values are expressed as approximations, by the use of "about," it will be understood that the particular value forms another embodiment. It will be understood that the endpoints of each of the ranges are significant both in relation to the other endpoint and independently of the other endpoint. It will also be also understood that there are a number of values disclosed herein, and that each value is also disclosed herein as "about" that particular value in addition to the value itself. For example, if the value "50" is disclosed, then "about 50" is also disclosed. It is also understood that when a value is disclosed that "less than or equal to" a value, that values "greater than or equal to the value" and possible ranges between values are also disclosed, as understood by one skilled in the art. For example, if the value "50" is disclosed, then "less than or equal to 50" and "greater than or equal to 50" are also disclosed. It is also understood that the throughout the application, data are provided in different formats, and it is understood that these data represent endpoints and starting points as well as ranges for any combination of the data points. For example, if a particular data point "50" and a particular data point "100" are disclosed, it is understood that greater than, greater than or equal to, less than, less than or equal to, and equal to 50 and 100 are considered disclosed as well as between 50 and 100.

As used herein, "amniotic fluid cells" mean cells that have been extracted, retrieved or derived from amniotic fluid from an amniotic sac of a pregnant female.

As used herein, "amniotic tissue" means amniotic fluid cells, placental membrane, amnion tissue or combinations thereof.

As used herein, the terms "optional" or "optionally" mean that the subsequently described event or circumstance may or may not occur, and that the description includes instances where said event or circumstance occurs and instances where it does not occur.

As used herein, the phrase "substantially all" refers to the maximum amount reasonably attainable by one skilled in the art.

As used herein, the term "particle size" means the particle size as determined, for example, by a laser scattering particle size distribution analyzer.

As used herein, the phrase "cartilage defect" refers to diseased cartilage, a void created within cartilage by the removal of at least a portion of diseased cartilage, or a void created by cartilage degeneration.

As used herein, the phrase "diseased cartilage" refers to cartilage that is damaged, degenerating, inflamed, necrotic, or otherwise showing symptoms thereof, such as pain, swelling, stiffness, and restraint of movement. Diseased cartilage may be diagnosed in several ways including, but not limited to, x-ray analysis, MRI analysis, or arthroscopy.

As used herein, the phrase "calcified cartilage" refers to the zone of cartilage that connects articular cartilage to the underlying subchondral bone.

As used herein, the phrases "placental membrane" or "amnion tissue" refer to one or more layers of the placental membrane. For example, placental membrane or amnion tissue may refer to a placental membrane comprising both the amniotic and chorionic layers. In another example, placental membrane or amnion tissue may refer to a placental membrane in which the chorion has been removed. In another example, placental membrane or amnion tissue may refer to a placental membrane in which the epithelial layer has been removed.

As used herein, the phrase "subchondral bone" refers to bone underlying cartilage. Subchondral bone may or may not be attached to the cartilage.

As used herein, the phrase "skeletal joint bone" refers to a bone in contact, or associated, with a skeletal joint. For example, a skeletal joint bone associated with the knee joint may include the femur.

As used herein, the phrase "chondrogenic differentiation" refers to the differentiation of one cell type into a chondrocyte or chondrocyte-like cell. For example, mesenchymal stem cells may undergo chondrogenic differentiation such that they differentiate into chondrocytes.

As used herein, the phrase "prenatal stem cell" refers to a cell originating from an embryonic or fetal mammalian organism and which is found in or isolated from a prenatal sample. The term "mammalian" as used herein, encompasses any mammal, for instance a human. A "prenatal sample" is defined herein as a prenatal fluid or tissue. The term "prenatal fluid" is defined as mammalian third trimester amniotic fluid. A "prenatal tissue" is the fetal component of a mammalian placental tissue, i.e., tissues originating predominantly from the fetus, for instance placental membranes. The prenatal stem cells of the present disclosure specifically exclude stem cells isolated or collected from an adult source, i.e., any maternal components or maternal tissue present in the mammalian placental membrane. A "stem cell" is a cell which has the potential to differentiate into multiple different cell types, and includes both multipotent and pluripotent cells.

As used herein, the terms "treatment" or "treating" include any desirable effect on the symptoms or pathology of a disease or condition, and may include even minimal reductions in one or more measurable markers of the disease or condition being treated. "Treatment" does not necessarily indicate complete eradication or cure of the disease or condition, or associated symptoms thereof. The subject receiving this treatment is any animal in need, including primates, in particular humans, and other mammals including, but not limited to, equines, cattle, swine, and sheep; and poultry and pets in general.

B. MAKING OF THE PLACENTAL MEMBRANE PREPARATION

1. Placental Membrane Preparation.

The placental membrane preparation includes amnion tissue and, optionally, amniotic fluid cells. The amnion tissue component of the placental membrane preparation is produced from placentas collected from consenting donors in accordance with the Current Good Tissue Practice guidelines promulgated by the U.S. Food and Drug Administration. In particular, soon after the birth of a human infant via a Cesarean section delivery, the intact placenta is retrieved, and the placental membrane is dissected from the placenta. Afterwards, the placental membrane is cleaned of residual blood, placed in a bath of sterile solution, stored on ice and shipped for processing. Once received by the processor, the placental membrane is rinsed to remove any remaining blood clots, and if desired, rinsed further in an antibiotic rinse [Diaz-Prado S M, et al. *Cell Tissue Bank* 11, 183-195 (2010)].

The antibiotic rinse may include, but is not limited to, the antibiotics: amikacin, aminoglycosides, amoxicillin, ampicillin, ansamycins, arsphenamine, azithromycin, azlocillin, aztreonam, bacitracin, capreomycin, carbacephem, carbapenems, carbenicillin, cefaclor, cefadroxil, cefalexin, cefalotin, cefamandole, cefazolin, cefdinir, cefditoren, cefepime, cefixime, cefoperazone, cefotaxime, cefoxitin, cefpodoxime, cefprozil, ceftaroline fosamil, ceftazidime, ceftibuten, ceftizoxime, ceftobiprole, ceftriaxone, cefuroxime, chloramphenicol, ciprofloxacin, clarithromycin, clindamycin, clofazimine, cloxacillin, colistin, cycloserine, dapsone, daptomycin, demeclocycline, dicloxacillin, dirithromycin, doripenem, doxycycline, enoxacin, ertapenem, erythromycin, ethambutol, ethionamide, flucloxacillin, fosfomycin, furazolidone, fusidic acid, gatifloxacin, geldanamycin, gentamicin, glycopeptides, grepafloxacin, herbimycin, imipenem or cilastatin, isoniazid, kanamycin, levofloxacin, lincomycin, lincosamides, linezolid, lipopeptide, lomefloxacin, loracarbef, macrolides, mafenide, meropenem, methicillin, metronidazole, mezlocillin, minocycline, monobactams, moxifloxacin, mupirocin, nafcillin, nalidixic acid, neomycin, netilmicin, nitrofurans, nitrofurantoin, norfloxacin, ofloxacin, oxacillin, oxytetracycline, paromomycin, penicillin G, penicillin V, piperacillin, platensimycin, polymyxin B, pyrazinamide, quinolones, quinupristin/dalfopristin, rifabutin, rifampicin or rifampin, rifapentine, rifaximin, roxithromycin, silver sulfadiazine, sparfloxacin, spectinomycin, spiramycin, streptomycin, sulfacetamide, sulfadiazine, sulfamethizole, sulfamethoxazole, sulfanilamide, sulfasalazine, sulfisoxazole, sulfonamidochrysoidine, teicoplanin, telavancin, telithromycin, temafloxacin, temocillin, tetracycline, thiamphenicol, ticarcillin, tigecycline, tinidazole, tobramycin, trimethoprim, trimethoprim-sulfamethoxazole (co-trimoxazole) (TMP-SMX), and troleandomycin, trovafloxacin, or vancomycin.

The antibiotic rinse may also include, but is not limited to, the antimycotics: abafungin, albaconazole, amorolfin, amphotericin B, anidulafungin, bifonazole, butenafine, butoconazole, caspofungin, clotrimazole, econazole, fenticonazole, fluconazole, isavuconazole, isoconazole, itraconazole, ketoconazole, micafungin, miconazole, naftifine, nystatin, omoconazole, oxiconazole, posaconazole, ravuconazole, sertaconazole, sulconazole, terbinafine, terconazole, tioconazole, voriconazole, or other agents or compounds with one or more anti-fungal characteristics.

The placental membrane may be processed to remove one or more particular layers of the membrane. The chorion may be removed from the placental membrane by mechanical means well-known to those skilled in the art. The chorion may be removed, for example, by carefully peeling the chorion from the remainder of the placental membrane using blunt dissection [Jin C Z, et al. *Tiss Eng* 13, 693-702 (2007)]. Removal of the epithelial layer from the placental membrane may be achieved using several methods well-known to those skilled in the art. The epithelial layer may be preserved or, if desired, may be removed by, for example, using trypsin to induce necrosis in the epithelial cells [Diaz-Prado S M, et al. *Cell Tissue Bank* 11, 183-195 (2010)]. Removal of the epithelial layer may comprise, for example, treatment with 0.1% trypsin-ethylenediaminetetraacetic acid (EDTA) solution at 37° C. for 15 minutes followed by physical removal using a cell scraper [Jin C Z, et al. *Tiss Eng* 13, 693-702 (2007)]. Preferably, the placental membrane utilized for the amnion tissue component of the placental membrane preparation is the amniotic membrane including the amniotic epithelial cell layers but excluding the chorion.

The placental membranes may be ground using techniques known in the art, and the resulting particles resuspended in a fluid or dried. Such processing may be carried out so as to preserve, to the extent possible, the protein content of the membrane, including growth factors. Preferably, grinding should be conducted under temperature controlled conditions, such as in a cryomill. Preferably such ground pieces of tissue should have a particle size of less than 1000 micrometers. Alternatively, the membranes may be minced using techniques known in the art, creating, e.g., small cubes of membrane tissue. Preferably such minced pieces of tissue should have particle sizes ranging from 0.1 mm to 3 mm. Minced tissue particles may be square, rounded, oblong or irregular in shape.

The ground or minced placental membrane includes amnion tissue containing organized amniotic extracellular matrix (ECM), amniotic tissue cells and growth factors contained within the ECM and amniotic tissue cells. The ECM includes amnion-derived collagen, fibronectin, laminin, proteoglycans and glycosaminoglycans. The amnion-derived collagen may derived from an epithelium layer, a basement membrane layer, a compact layer, a fibroblast layer, an intermediate layer and a spongy layer of the amnion tissue.

The placental membrane preparation may be combined with prenatal stem cells if desired. For example the preparation may include amniotic fluid cells that are derived from amniotic fluid that is collected during amniocentesis or scheduled C-section from consenting donors. The amniotic fluid is spun thereby pelletizing the amniotic fluid cells. The resulting amniotic fluid cells may be combined with ground placental membrane and cryopreserved in a solution containing approximately 5 to 10% vol/vol Dimethyl Sulfoxide (DMSO) and 15 to 25% vol/vol protein, with the balance being crystalloids. Suitable dosages of the placental membrane preparation range from between about 0.25 ccs to about 5 ccs, depending on the amount of diseased or damaged tissue.

Minced or ground membrane particles may be freeze dried and sterilized, or stored in a cryopreservative or hypothermic storage solution allowing the preservation of the viability of some membrane cells. A suitable ground placental membrane preparation, which includes amniotic fluid cells, is sold by NuTech Medical, Inc. of Birmingham, Ala. under the name NuCel™.

The placental membrane preparation may include a processed cartilage selected from the group consisting of a ground cartilage, a minced cartilage, a cartilage paste and combinations thereof. The processed cartilage may be an autograft cartilage, an allograft cartilage or combinations thereof. When processed cartilage is added to a minced or ground placental membrane preparation, the processed cartilage is preferably provided in between a 3:1 and a 1:3 ratio by volume to the original membrane preparation.

The placental membrane preparation may include hyaluronic acid, saline or a combination thereof. Hyaluronic acid and saline may be included with the placental membrane preparation when it is desired to inject the preparation into a skeletal joint. When hyaluronic acid or saline is added to a placental membrane preparation, the hyaluronic acid or saline is preferably provided in a 2:1 or 1:1 ratio by volume to the original membrane preparation.

The placental membrane preparation may include one or more biocompatible glues. Biocompatible glues are natural polymeric materials that act as adhesives. Biocompatible glues may be formed synthetically from biological monomers such as sugars and may consist of a variety of substances, such as proteins and carbohydrates. Proteins such as gelatin and carbohydrates such as starch have been used as general-purpose glues by man for many years. Preferably, the biocompatible glue is fibrin glue, such as Tisseel. Fibrin is made up of fibrinogen (lyophilised pooled human concentrate) and may also include thrombin (which may be reconstituted with calcium chloride).

C. USES OF THE PLACENTAL MEMBRANE PREPARATION

The embodiments of the placental membrane preparation, described herein, may be used to regenerate damaged or defective cartilage or disc tissue. Preferably, the embodiments of the placental membrane preparation, described herein, may be used to repair hyaline articular cartilage in vivo. Alternatively, in cases of meniscal defects of the knee the preparations may be used in conjunction with meniscal repair or partial meniscectomy to repair defects in the meniscal cartilage. Alternatively, in cases of degenerated intervertebral discs the preparations may be used to restore disc height and function. The compositions and methods pertaining to the placental membrane preparation may be used in a number of clinical conditions including, but not limited to, chondral defects, meniscal defects or tears, osteoarthritis, traumatic injury, such as rotational or compaction injuries, osteochondritis dessicans, pathological injury, age-related degeneration, and other defects affecting skeletal joints, in particular cartilage. Such techniques may be used to address pathologies of the knee, shoulder, ankle, spine and other skeletal joints.

The membrane and glue preparation, with or without cartilage, may be placed into a hyaline articular cartilage defect after a marrow stimulation procedure. Alternatively, the preparation may be placed in a meniscal defect prior to a defect repair via suture or other fixation techniques, or may be placed into the defect created by a partial meniscectomy. The preparation may be placed in a degenerated intervertebral disc. The preparation may be placed in a minimally invasive manner via a syringe or arthroscopic cannula.

The ground membrane particles may be injected into the joint capsule after a marrow stimulation procedure has been completed to stimulate the development of reparative articular cartilage. Such injections may be repeated several times at subsequent time periods if desired. The particles may be combined with a biocompatible carrier such as saline or hyaluronic acid prior to injection.

Articular cartilage can be generated in vivo in a skeletal joint by conducting a marrow stimulation procedure, and then placing in the defect a preparation of ground or minced amniotic membrane and a biocompatible glue. Ground or minced autograft or allograft cartilage may also be included in the preparation. The method may be carried out in a minimally invasive manner using arthroscopic techniques.

Meniscal cartilage can be generated in vivo by conducting a partial meniscectomy procedure, and then placing in the defect a preparation of ground or minced amniotic membrane, which may be mixed with or covered by one or more biocompatible glues. Ground or minced autograft or allograft cartilage may also be included in the preparation. The method may be carried out in a minimally invasive manner using arthroscopic techniques.

A tear or defect in meniscal cartilage can be repaired in vivo in a skeletal joint by placing in a meniscal tear or defect a preparation of ground or minced amniotic membrane with or without a biocompatible glue, followed by repairing of the tear or defect using suture or another fixation method. The method may be carried out in a minimally invasive manner using arthroscopic techniques.

A degenerated intervertebral disc can be regenerated by inserting minced amniotic membrane into the disc, with or without the addition of biocompatible glue, and then closing any resulting opening in the disc using biocompatible glue or other closure means.

The minced placental membrane in the placental membrane preparation may contain living multi-potent prenatal cells if fresh or cryopreserved preparations are used. The minced membrane may also act as a scaffold or matrix for cell engraftment and in-growth. Thus, the minced membranes act as an integral matrix with cells intact in their normal location, i.e., sessile cells, and without culturing. The minced placental membranes also provide a reservoir of growth factors attracting incoming blood-born mesenchymal cells (MSCs), chondrocytes, and other reparative cells. In contrast, the ground placental membrane in the preparation includes particles that may be too small to allow for cell in-growth. However, it is believed that the small particle sizes provides the placental membrane preparation with a larger placental membrane surface area than surface area provided by minced placental membrane and thus, and may permit faster release of growth factors than the minced membrane. It is further believed that the small particle sizes allow for viable placental tissue cells to exist within the preparation.

Once applied to a cartilage defect or degenerated disc, the multi-potent amniotic cells, including those that are sessile and native to the placental membrane sheet, may chondrogenically differentiate in vivo. The amniotic cells and the growth factors contained in the cells may also stimulate migration, differentiation, proliferation and matrix deposition by the patient's own cells.

D. EXAMPLE

The use of human amniotic allograft for treating osteo chondritis dissecans of the talar dome was observed.

Patients and Methods

Patients were selected from persons who had undergone arthroscopy with micro-fracture technique for treatment of a talar dome lesion less than 2 $cm^2$. Ankle scopes of 832 patients were reviewed. Three hundred and forty-five of those patients had lesions that were less than 2 $cm^2$ on the talar dome. Patients were excluded from the study based on lack of availability of MRI scans, absence of solitary and isolated lesions, insufficient follow up times and whether patients had other major surgeries such as a peroneal tendon relocation or significant tibial, fibular, or talar exostectomy not done arthroscopically at the same time as the lesion repair. To be included in the study, a patient's trans-chondral fracture (TCF) had to be reachable via arthroscopy and not composed of a multi-planar shoulder lesion of the talus. All patients had modified American College of Foot and Ankle Surgeons (ACFAS) scores and visual analog scores (VAS) taken preoperatively and postoperatively at 3 months, 12 months and 24 months. The patients had MRI scans of lesions on their talar dome and did not have any other major surgeries at the time of surgically repairing the lesion.

After exclusions, the human amniotic allograft (HAA) group included 54 patients with a talar dome lesion less than 2 cm2 whose treatment included a human amniotic allograft to assist in healing and regeneration of cartilage. The control group consisted of 47 patients that had a talar dome lesion less than 2 $cm^2$ in size with no HAA allograft use. All patients had to complete four weeks of post-operative physical therapy. Patients were not randomized or blinded to the use of HAA.

Surgical Technique

Standard medial and lateral portals were used, standardized with a uniform distraction technique. The ankle had an inspection, and then a generalized synovectomy as indicated was done. As needed, a medial to lateral debridement and exostectomy of the anterior lip of the tibia was performed. Care was taken to assure that the tibial-talar interface had no residual kissing lesion remaining. The talar dome lesion was identified and compared to x-ray and MRI size and location. A circumferential debridement was performed to the subchondral level. A micro-fracture awl standard technique was used to perform micro-fracturing of the lesion. When used, liquid form HAA was used and applied directly to the lesion via needle technique and under direct visualization. Instruments were removed and portals were closed.

Human Amniotic Allograft (HAA) Information

The specific HAA material used on the patient population was 2 ccs of a cryopreserved liquid form of amniotic allograft available from NuTech Medical, Inc. of Birmingham, Ala. and sold under the name NuCel®. NuCel® contains morselized amniotic membrane as well as other cells in the amniotic fluid of amniotic origin.

Results

The average physical therapy for the control group pre-operatively was 5.0 weeks and 5.7 weeks post-operative. The average for the treatment group was 3.9 weeks preoperatively and 4.6 weeks postoperatively. There were no significant differences between the control and treatment groups' pre-operative and post-operative weeks in physical therapy (p=0.011 pre-operative, p=0.08 post-operative) as shown in Table 1.

TABLE 1

Patient Demographics with averages and p-values

| | | Physical Therapy (weeks) | | VAS pain score Average | | ACFAS Score | | |
|---|---|---|---|---|---|---|---|---|
| | Age | Pre-op | Post-op | Pre-op | Post-op (24 months) | Pre-op | 3 month | 12 month | 24 month |
| Graft | 47.39 | 3.86 | 4.66 | 5.18 | 1.23 | 73.39 | 89.53 | 91.14 | 88.26 |
| No Graft | 46.01 | 5.09 | 5.74 | 5.02 | 2.48 | 74.39 | 84.7 | 86.19 | 83.93 |
| p values | | | | | | | | | |
| Comparing* | 0.3517 | 0.082 | 0.011 | .353 | 7E-6 | .293 | 5E-8 | 1E-9 | 4E-5 |
| Graft** | | | | | 1E-23 | | 8E-23 | 4E-26 | 1E-28 |
| No Graft** | | | | | 2E-14 | | 5E-8 | 1E-9 | 4E-5 |

*p value comparing the category of the graft group to the same category of non-graft group
**p value comparing the post-operative score to the pre-operative score.

The average VAS scores for the control and HAA groups were 5.0 and 5.2 pre-operatively, respectively and 2.5 and 1.2 at 24 months post-operatively, respectively. There was no significant differences between the pre-operative VAS scores (p=0.35) but a significant difference in the post-operative VAS scores (p<0.001) was observed. There was also significance when comparing the pre and post-operative scores together for the control group and HAA group (p<0.001, p<0.001 respectively), as shown in Table 1.

The ACFAS averages for the control and HAA groups were 74.4 and 73.4 for preoperative, 84.7 and 89.5 at 3 months follow up, 86.2 and 91.1 at 12 months follow up and 83.9 and 88.3 at 24 months follow up. The ACFAS scores were not significant between the control and HAA pre-operative numbers (p=0.293) but significant when comparing the control and HAA ACFAS scores at 3 months, 12 months and 24 months post-operatively (p<0.001, p<0.001, p<0.001 respectively), as shown in Table 1. The total patient average width of the defect or bone edema from MRI scans was 1.9 cm but 1.3 cm intra-operatively. There was an average difference of 0.6 cm between the MRI and intra-operative size of the defect, with the MRI findings showing larger or equal in all but one case (p<0.001).

REFERENCES

1. Boo L, et al., A preliminary study of human amniotic membrane as a potential chondrocyte carrier, *Malay Orthop J* 3, 16-23 (2009).
2. Davis, J S, Skin transplantation with a review of 550 cases at the Johns Hopkins Hospital, *John Hopkins Med J* 15, 307 (1910).
3. Diaz-Prado S M, et al., Cell therapy and tissue engineering to regenerate articular cartilage, in BIOMEDICAL ENGINEERING, TRENDS, RESEARCH AND TECHNOLOGIES (Komorowska M A & Olsztynska-Janus S, eds.), pp. 193-216 (2011).

4. Diaz-Prado S M, et al., Potential use of the human amniotic membrane as a scaffold in human articular cartilage repair, *Cell Tissue Bank* 11, 183-195 (2010).
5. Fiorentino G., et al., Easy and Safe All-Inside Suture Technique for Posterior Horn Tears of Lateral Meniscus Using Standard Anteromedial and Anterolateral Portals. Arthroscopy Techniques, Vol 2, No 4 (November), 2013: pp e355-e359.
6. Hildner F, et al., State of the art and future perspectives of articular cartilage regeneration: a focus on adipose-derived stem cells and platelet-derived products, *J Tissue Eng Regen Med* 5, e36-e51 (2011).
7. Jin C Z, et al., Human amniotic membrane as a delivery matrix for articular cartilage repair, *Tiss Eng* 13, 693-702 (2007).
8. Kanthan S R, et al., The different preparations of human amniotic membrane (HAM) as a potential cell carrier for chondrocytes, *Eur Cell Mater* 20, 1 page (2010).
9. Kon, E. et al., Tissue Engineering for Total Meniscal Substitution: Animal Study in Sheep Model—Results at 12 Months. *Tissue Eng Part A*. 2012 August; 18(15-16): 1573-82.
10. Krishnamurithy G, et al., Human amniotic membrane as a chondrocyte carrier vehicle/substrate: in vitro study, *J Biomed Mater Res Part A* 99A, 500-506 (2011).
11. Lindenmair A, et al., Osteogenic differentiation of intact human amniotic membrane, *Biomaterials* 31, 8659-8665 (2010).
12. Mermet I, et al., Use of amniotic membrane transplantation in the treatment of venous leg ulcers, *Wound Repair and Regeneration* 15, 459 (2007).
13. Mithoefer, K et. al., Chondral resurfacing of articular cartilage defects in the knee with the microfracture technique. Surgical technique. *J Bone Joint Surg Am*. 2006 September; 88 Suppl 1 Pt 2:294-304.
14. Moriya T, et al., Evaluation of reparative cartilage after autologous chondrocyte implantation for osteochondritis dissecans: histology, biochemistry, and M R imaging, *J Orthop Sci* 12, 265-273 (2007).
15. Niknejad H, et al., Properties of the amniotic membrane for potential use in tissue engineering, *Eur Cell Mater* 15, 88-99 (2008).
16. Park, S. H., et. al., Intervertebral Disk Tissue Engineering Using Biphasic Silk Composite Scaffolds. *Tissue Eng. Part A*, (2012) 18(5-6):447-458
17. Scotti C. et al., Meniscus Repair And Regeneration: Review On Current Methods And Research Potential. European Cells and Materials Vol. 26 2013, 150-170.
18. Wilshaw S P, et al. Production of an acellular amniotic membrane matrix for use in tissue engineering, *Tiss Eng* 12, 2117-2129 (2006).
19. Xing, L. et al., Microfracture combined with osteochondral paste implantation was more effective than microfracture alone for full-thickness cartilage repair. *Knee Surg Sports Traumatol Arthrosc* (2013) 21:1770-1776.
20. Zhou S, et al., Demineralized bone promotes chondrocyte or osteoblast differentiation of human bone marrow stromal cells cultured in collagen sponges, *Cell Tissue Bank* 6, 33-44 (2005).
21. U.S. Pat. No. 7,824,711.
22. U.S. Pat. No. 6,063,094.
23. U.S. Pat. No. 5,612,028.
24. U.S. Pat. No. 5,004,468.
25. U.S. Pat. No. 3,640,279.
26. U.S. Pat. No. 3,472,228.
27. U.S. Pat. No. 3,358,688.
28. U.S. Patent Application Publication No. 2003-0187515.
29. U.S. Patent Application Publication No. 2004-0161419.

What is claimed is:

1. A method of generating cartilage in vivo in a skeletal joint comprising,
   cryopreserving a combination including amniotic fluid cells and a ground placental membrane material in a cryopreservative solution containing 5% to 10% by volume dimethyl sulfoxide and 15% to 25% by volume protein with a balance of crystalloids,
   forming a preparation from the combination, the preparation including the amniotic fluid cells and the placental membrane material, and
   applying the preparation to a cartilage defect preparation to generate hyaline cartilage within the skeletal joint in vivo.

2. The method according to claim 1 comprising adding to the preparation a processed cartilage selected from the group consisting of a ground cartilage, a minced cartilage, a cartilage paste and combinations thereof.

3. The method according to claim 2 wherein the processed cartilage is selected from the group consisting of an autograft cartilage, an allograft cartilage and combinations thereof.

4. The method according to claim 1 comprising adding to the preparation hyaluronic acid, saline or a combination thereof.

5. The method according to claim 1 wherein the ground placental membrane material exhibits an average particle size of less than 0.1 mm.

6. The method according to claim 1 wherein the preparation includes the minced placental membrane and the minced placental membrane exhibits an average particle size within a range of 0.1 mm to 3 mm.

7. The method according to claim 1 wherein the placental membrane material includes amnion tissue containing organized amniotic extracellular matrix (ECM), amniotic tissue cells and growth factors contained within the ECM and amniotic tissue cells.

8. The method according to claim 7 wherein the ECM includes amnion-derived collagen, fibronectin, laminin, proteoglycans and glycosaminoglycans.

9. The method according to claim 8 wherein the amnion-derived collagen is derived from an epithelium layer, a basement membrane layer, a compact layer, a fibroblast layer, an intermediate layer and a spongy layer of the amnion tissue.

10. The method according to claim 1 wherein the preparation is injected into the cartilage defect.

11. The method according to claim 1 wherein the preparation is introduced to the cartilage defect using a minimally invasive procedure or through an arthroscopic cannula.

12. The method according to claim 1 wherein the preparation is injected into a joint capsule of the skeletal joint after a marrow stimulation procedure has been performed for stimulating the development of a reparative cartilage in the skeletal joint.

13. The method according to claim 12 further comprising, following injecting the preparation into the joint capsule, evaluating the amount of in vivo cartilage generation within the skeletal joint, and based thereon, determining whether additional injections of the preparation into the joint capsule are desired for accomplishing a desired amount of in vivo cartilage generation within the skeletal joint.

14. The method according to claim 1 comprising adding to the preparation a biocompatible glue.

15. The method according to claim 1 wherein the cartilage defect is a hyaline articular cartilage defect.

16. The method according to claim 1 further comprising causing blood to accumulate within the cartilage defect.

17. The method according to claim 16 wherein the blood forms a clot within the cartilage defect.

18. The method according to claim 16 wherein the blood originates from subchondral bone located adjacent to the cartilage defect.

19. The method according to claim 16 wherein the preparation is introduced to the cartilage defect following accumulation of the blood within the cartilage defect.

20. The method according to claim 1 further comprising performing a marrow stimulation technique in the skeletal joint.

21. The method according to claim 1 wherein the cartilage defect is a meniscus cartilage defect.

22. The method according to claim 1 wherein the preparation excludes in vitro cultured cells.

23. The method according to claim 1 wherein the preparation excludes in vitro cultured chondrocytes.

24. The method according to claim 1 wherein the preparation promotes the regeneration of cartilage in the cartilage defect in the absence of in vitro cultured cells.

25. The method according to claim 1 further comprising removing diseased cartilage from the skeletal joint thereby forming a void into which the preparation is introduced.

26. The method according to claim 25 wherein substantially all of a healthy cartilage in the skeletal joint remains in the skeletal joint after the diseased cartilage is removed.

27. The method according to claim 1 wherein the preparation excludes a synthetic matrix material.

28. The method according to claim 1 wherein the preparation is substantially free of chondrocytes immediately prior to introduction to the cartilage defect.

29. The method according to claim 1 wherein a plurality of cells contained within and native to the placental membrane material chondrogenically differentiate in vivo within the cartilage defect.

30. The method according to claim 29 wherein the plurality of cells include mesenchymal cells.

31. The method according to claim 1 wherein the cartilage defect is an intervertebral disc defect.

32. The method of claim 1 comprising cryopreserving the combination.

33. The method of claim 1 comprising cryopreserving the combination in a solution containing dimethyl sulfoxide.

34. The method of claim 1 comprising cryopreserving the combination in a solution containing approximately 5% to 10% by volume dimethyl sulfoxide.

35. The method of claim 1, wherein the cryopreservative solution contains 10% by volume dimethyl sulfoxide.

36. The method of claim 1 wherein the amniotic fluid cells are viable.

37. The method of claim 1 comprising in vivo chondrogenic differentiation of the amniotic fluid cells.

* * * * *